(12) United States Patent
Haaja et al.

(10) Patent No.: US 9,474,612 B2
(45) Date of Patent: Oct. 25, 2016

(54) IMPLANTABLE TREATMENT DEVICE FIXED OR INTERLINKED TO BONE

(75) Inventors: Juha Kalevi Haaja, Epsoo (FI); Harri Olavi Hallila, Espoo (FI); Antti Gabriel Ritvanen, Espoo (FI)

(73) Assignee: Synoste Oy, Espoo (FI)

( * ) Notice: Subject to any disclaimer, the term of this patent is extended or adjusted under 35 U.S.C. 154(b) by 113 days.

(21) Appl. No.: 13/697,654

(22) PCT Filed: May 23, 2011

(86) PCT No.: PCT/FI2011/050465
§ 371 (c)(1),
(2), (4) Date: Apr. 29, 2013

(87) PCT Pub. No.: WO2011/148047
PCT Pub. Date: Dec. 1, 2010

(65) Prior Publication Data
US 2014/0005788 A1    Jan. 2, 2014

(30) Foreign Application Priority Data

May 24, 2010 (FI) ...................................... 20105569

(51) Int. Cl.
*A61B 17/68* (2006.01)
*A61F 2/30* (2006.01)
*A61B 17/66* (2006.01)
*A61B 17/72* (2006.01)

(52) U.S. Cl.
CPC ............... *A61F 2/30* (2013.01); *A61B 17/666* (2013.01); *A61B 17/68* (2013.01); *A61B 17/7216* (2013.01)

(58) Field of Classification Search
CPC    A61B 17/66; A61B 17/68; A61B 2017/681; A61B 17/7216
USPC .......... 606/57–58, 258, 62–63, 282, 90, 105
See application file for complete search history.

(56) References Cited

U.S. PATENT DOCUMENTS

| 4,453,539 A | 6/1984 | Raftopoulos et al. |
| 5,415,660 A | 5/1995 | Campbell et al. |
| 5,704,939 A | 1/1998 | Justin |
| 6,706,042 B2 * | 3/2004 | Taylor ............................. 606/57 |
| 2002/0143344 A1 | 10/2002 | Taylor |
| 2007/0015622 A1 | 1/2007 | Stauch |
| 2009/0076597 A1 * | 3/2009 | Dahlgren et al. .............. 623/2.1 |

FOREIGN PATENT DOCUMENTS

| WO | WO 02/094113 A1 | 11/2002 |
| WO | WO 2009/115645 | 9/2009 |

* cited by examiner

*Primary Examiner* — Eduardo C Robert
*Assistant Examiner* — Julianna N Harvey
(74) *Attorney, Agent, or Firm* — Womble Carlyle Sandridge & Rice LLP (57) ABSTRACT

The invention relates to an implantable device fixed or interlinked to bone, which generates unidirectional movement by a member generating reciprocating motion in the same direction using means allowing unidirectional movement. In the device, the means allowing unidirectional movement comprise means based on friction which make line contact.

9 Claims, 4 Drawing Sheets

IMPLANTABLE TREATMENT DEVICE FIXED OR INTERLINKED TO BONE

BACKGROUND

1. Field of the Disclosure

The invention relates to the details of an implantable treatment device, especially to means allowing unidirectional movement, by means of which the short movement of a material generating reciprocating motion is converted into unidirectional long movement.

2. Description of Related Art

Prior art is represented, for example, by the same applicant's earlier application FI20085238. The background information on bone extension treatments disclosed therein also applies to the device of the present invention.

SUMMARY OF THE DISCLOSURE

The aim of the invention is to provide a device suitable for implantable use which functions even better, by means of which a change in the distance between two attachment points can be achieved with repeated changes in the length of intelligent material. Achieving sufficient power generation from the short reciprocating motion provided by the magnetostrictive material has proven to be a problem in connection with the above-mentioned application. The means allowing unidirectional movement and the clearances of the entire device must be smaller than the change in length effected by the magnetostrictive material when sufficient power is generated.

Magnetostrictive material is advantageous because it provides sufficient power, for example, in bone extension treatment. The small length of the reciprocating motion generated is, however, a problem, whereby high demands are made on the means allowing unidirectional movement. Magnetostrictive material does not require any electronics around it. Thermal memory metal, such as Nitinol, requires heating means and a power feed and control means for them. MSM (Magnetic Shape Memory) materials generate a larger movement than magnetostrictive materials, but their power generation is insufficient without mechanical transmission. A piezoelectric actuator, on the other hand, requires, for example, an induction coil to generate the required voltage. All of the above intelligent materials can, however, be used in connection with the present invention with limitations.

The distraction osteogenesis application according to the invention generally requires the following of power transmission:

(1) The movement must be carried out in a controlled manner in steps of 0.25 mm (0.25 mm four times per day, that is, 1.0 mm/day).
(2) The power transmission must transmit the power required for the distraction.
(3) The movement must be locked after the step.
(4) The locking must withstand the static and dynamic mechanical stress transmitted from the limb.

In addition, the selected treatment method, that is, medullary nailing, sets special requirements:

(5) Power transmission must fit inside the medullary nail.
(6) The materials used must be biocompatible or their sufficient isolation from the body must be possible.

With Terfenol-D, a reciprocating, repeated motion of about 0.15 mm is achieved during the extension treatment of a leg. This corresponds to a 0.12% length extension with the counterforce required for treatment. Terfenol is brittle and thus no twisting, turning or cutting forces may be exerted on it. In the light of current knowledge, most patients could be treated with an extension force of approximately 800 N. At lowest, extension has been achieved with 300 N, but at highest, the force required has been 1400 N. In connection with the extension treatment of leg bones, the maximum forces normally occurring during the use of the device are in turn of the order of 2.5 times the weight of the patient. The strain exerted on the device when the patient walks is at its greatest at the final stage of treatment when the telescope of the nail is at its longest and the length of the telescope is no longer increased, and the friction surfaces of the mechanism thus remain in place and the strain is exerted on the same point for several months. The healed bone and the leg muscles quite soon take on a large proportion of the longitudinal strain, whereupon mainly forces resisting torsion remain for the device to support.

In the earlier application was disclosed the use of a combination of a ball nut and a freewheel clutch and, for example, the use of barbs as means for allowing unidirectional movement. Furthermore, the publication US2009076597 (paragraph 0022 FIG. 2C) discloses the use of a clutch operated by wedging balls in connection with an orthopaedic or similar device. The application does not disclose a bone extension device, but applications in which the forces required are considerably lower.

The round wedging balls generate a high surface pressure which causes elastic and plastic deformation in parts of the clutch. This in turn forms a clearance in the clutch, which is the greater the higher the force to be resisted by one ball. Since the space available is extremely limited, large balls do not fit in the device, nor does a large number of ball clutches. The solution described in US2009076597 is, therefore, unsuitable for an application in which the forces are high and the space available is limited. The solution does not function in a bone distraction device, at least not when made of the usual materials, for example the materials conventionally used in ball bearings are not sufficiently durable for the device to withstand the strain for the duration of the whole treatment.

According to the invention, the wedge means making line contact is used for locking the return movement of a unidirectional means. This wedge means may be, for example, a roll or a sprag. A ball or a barrel-shaped means is also possible if its mating surfaces are appropriately designed.

On the basis of tests carried out by the inventor, several successive clutches allowing unidirectional movement reduce the clearance subject to strain and with a suitable implementation, the amount of the clearance is almost inversely proportional to the number of the means.

BRIEF DESCRIPTION OF THE SEVERAL VIEWS OF THE DRAWINGS

The solutions according to the invention are described in greater detail in the following, by means of the accompanying drawings.

DETAILED DESCRIPTION OF THE DISCLOSURE

Figure 1:
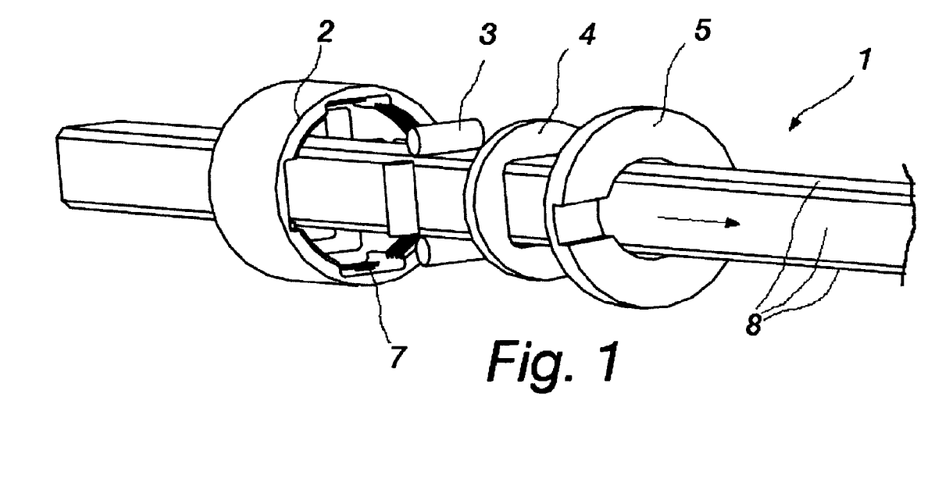
FIG. 1 shows an embodiment of the means of the device according to the invention allowing unidirectional movement.

FIG. 1 shows an exploded view of a device allowing unidirectional movement. The device may preferably comprise several wedge members in succession. In the Figure, the rod 1 moves inside the body 2, the rolls 3 rest on the slanted surfaces 7 pushed by a resilient plate 4 acting as a spring when the stopper 5 is screwed in place. When the rod is moved against the direction indicated by the arrow, the slanted surfaces 7 press the rolls 3 against the faces 8 of the rod, whereupon the rolls lock the rod in place. Several successive wedges or rolls may be constructed, for example, in such a way that the successive parts which wedge the rolls or balls at an inclined or slanted angle with respect to the direction of travel of the periphery are worked on joint unattached pieces which fit on the mating surface of the outer or inner part of the device. The slanted surfaces 7 are then worked into strips and several successive rolls are arranged on them. A spring is in this case provided for each roll, whereby the spring may rest on the surfaces of the strips or the springs may be pushed by means of the stopper 5 with means which extend, for example, beyond the space between the ends of the rolls 3. As a spring may also be used a polymer, for example, biocompatible silicone rubber, with which the rolls are glued in place on the separate strips.

In the preferred embodiment of FIG. 1 is used an angular rod 1 having, for example, a rectangular cross-section, on which the rolls rest pressed by the means 4 acting as a spring in such a way that the spring presses the rolls into the gap between the slanted surface and the rod. This spring means may be, for example, a biocompatible foamed plastic sheet or, for example, a silicone rubber spring made of a polymer, or a metal spring. A metal spring may be a bent, sheet-like coil spring, cup spring, etc. From the point of view of manufacturing technique, it is easiest to make the rod comprise surfaces which are straight in cross-section, because in that case the rolls or sprags are of uniform thickness and easy to manufacture. The rolls may also be, for example, barrel-shaped, but in that case the mating surfaces must be made concave. A barrel-shaped roll or a sprag having a friction surface in the shape of a circular arch makes possible line contact also with the inner surface of a round outer tube. In that case, however, the counterpart on the inner rod must be designed so as to be concave so that its radius of curvature will be the same as that of the outer tube. The concave and slanted mating surface can be made as a separate piece or it can be worked, for example, on the surface of the angular central rod.

Figure 2:
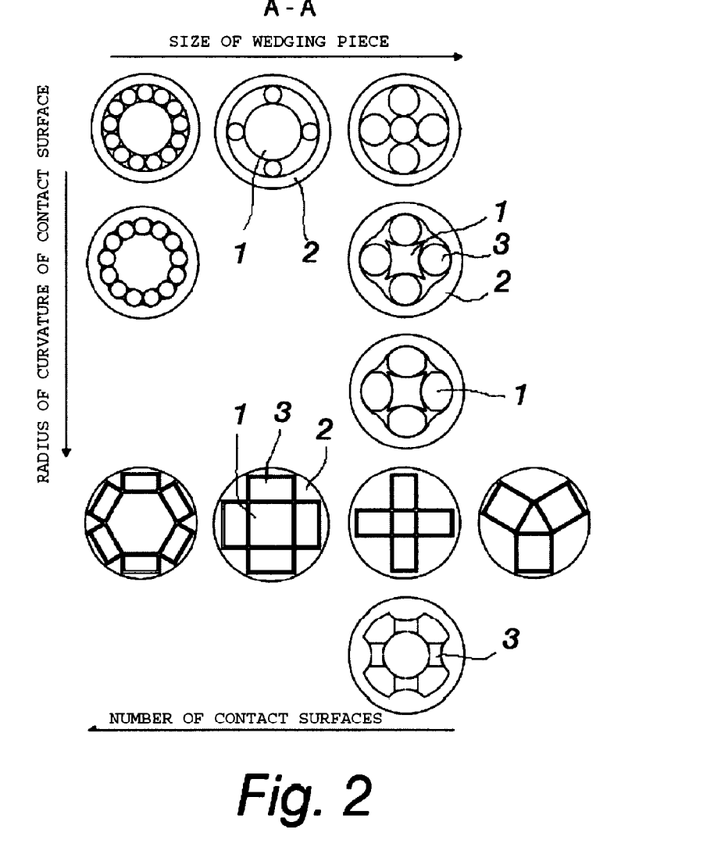
FIG. 2 shows different cross-sections for the device allowing unidirectional movement.

Instead of straight rolls can also be used wedges, balls or barrel-shaped rolls. Different alternatives are shown in FIG. 2, where the topmost row depicts means producing a point-form friction surface, which are not advantageous, for the reasons disclosed above, for example, in bone extension devices, because when constructed in the space available, their operation has proven unsatisfactory. The example in the third row depicts four barrel-shaped wedges or rolls. If barrel-shaped rolls are used, for example, with six or more rolls, an essentially round outer tube can be used.

Using a part comprising a separate slanted plane makes it possible to work the slanted parts which wedge the balls or rolls separately, for example, by means of laser or water cutting or chasing. Moreover, the separate part is only subjected to compressive forces and to some extent shearing forces, but hardly any tensile stress. The separate part can thus be made of a material which is optimal for use as a wedging slanted plane, which separate part can also be constructed in such a way that the slanted planes or counterparts of the wedge are constructed of separate smaller pieces, for example, by making only the slanted parts supporting the rolls or balls, for example, of tungsten carbide or titanium nitride, in which case they can be, for example, welded ultrasonically to a thin metal sheet which acts as a part supporting the rolls, balls or wedges and keeping them in place. Alternatively, the parts can be welded directly on the inner rod or outer tube. Using separate parts also makes it possible to use, for example, a round rod as a rod 1 in such a way that the separate parts are fitted on the surface of the rod, in which case the slanted surfaces are thus on the inner rod and lock the friction surfaces on the surface of the outer tube. In this case can also be used barrel-shaped rolls, the longitudinal curvature of which corresponds to the curvature of the inner surface of the outer tube. In the inner tube are in this case fitted separate parts comprising slanted surfaces either in such a way that they rest directly on the round rod or that straight mating surfaces are bevelled for them. In both cases, the advantage is easier workability of the inner rod itself, whereby the parts comprising special-shaped slanted surfaces can be made, for example, in large series by casting.

The separate part may preferably be rectangular or also a circular arch in cross-section, in which case its mating surface is the outer surface of the rod or the inner surface of the tube. The separate part may then be, for example, a tubular part made of metal sheet, possibly left open, which clamps onto the inner rod or outer tube by means of its own spring force. I this case the separate part is thus preferably made straight and rolled into a slightly larger or smaller open tube than its mating surface so that it settles tightly on its mating surface. The final formation against the outer tube or inner tube takes place only when forced by the balls, rolls or wedges. The separate part may be, for example, a thin steel plate with parts holding sintered balls, or the separate part is a plate with holes or cavities for balls. The separate part does not move with respect to its base during operation.

The separate pieces are locked, for example, by means of the stopper of FIG. 1, in the longitudinal direction and at the same time, also during locking, the frictional force keeps the parts in place against the surface of the outer part. The advantage of the separate part comprising a circular segment is that a round tube can be used on the inner or outer surface, or grooves having the correct cross-sectional shape can be worked for the balls on separate rails or, for example, in hard metal pieces comprising slanted grooves wedging the rolls, which are further welded or soldered on a tubular, longitudinally open sleeve holding them, which finally tightens against the surface when pressed by the locking means. In this way is avoided the machining of several slanted cylindrical surfaces on the inner surface of the tube and the material of the slanted parts themselves may be selected freely. Thus, the slanted surface can be made, for example, of ceramics or tungsten carbide, and its support and other parts, for example, of stainless steel or titanium. Thus, a hard and compression-resistant material can be used against the roll. The second mating surface of the roll or sprag is thus less resilient and more durable than when made of one material. The second mating surface is mobile and thus its plastic deformation is less disadvantageous, because in each operating cycle the roll presses a new point and the counter-tube of the device does not have to be used many times, because the device is usually patient-specific and the mechanics are, therefore, usually for single use only.

Slanted surfaces are easier to work on a small separate part, because in that case sintering can also be used as well as techniques known from car tyre studs and the drill bits of rock drills. Also, for example, electrolytic growing and spark machining are easier to carry out on unattached parts than directly on the surface of a telescopic tube. The separate part may be a thin metal strip or a thin strip also comprising vertical walls on which the spring means can rest. The spring means may be, for example, a metal spring or a polymer spring which at the same time acts as an adhesive during assembly.

Figure 4:
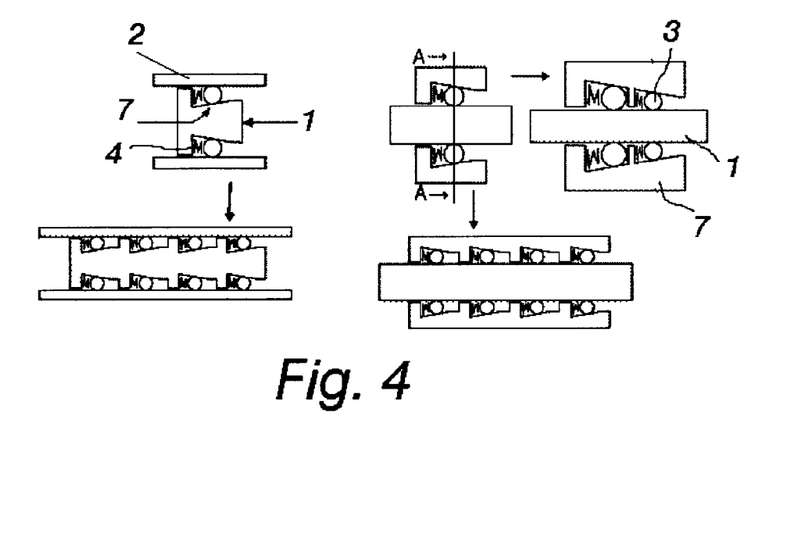
FIG. 4 shows views in principle of a freewheel operating on rolls.

FIG. 4 shows various alternative structures for internal and external locking devices operating with rolls, balls or barrel-shaped pieces. FIG. 2 shows different alternatives of section A-A.

Figure 5:
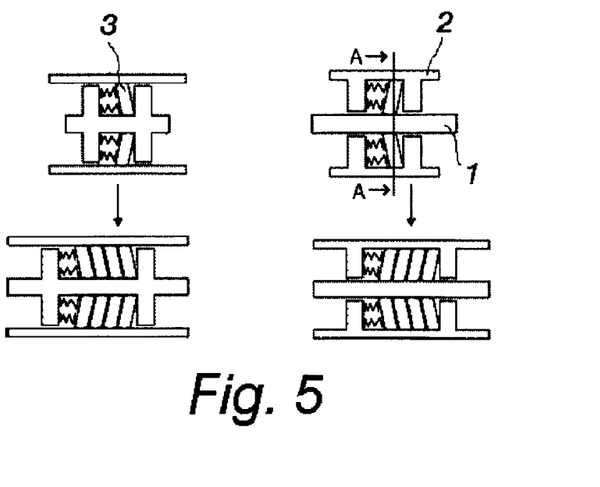
FIG. 5 shows the principle of a sprag clutch with linear movement.

FIG. 5 shows different sprag constructions. Deviating from FIG. 5, there may also be several springs for the sprags, in which case the plastic deformations formed in the structure do not generate biasing forces of different magnitudes to the wedges biased with a joint spring. There may also be springs between the wedges, in which case the spring may be thin and have a small length of stroke, whereby it allows a small angular difference between the wedges without the wedges losing their biasing force. Deviating from the Figure, there may be springs on both sides, in which case the different ends of the wedge are biased in different directions. Each wedge may also have a shaped mating surface at the immobile end.

The rolls 3 may be adhered by means of a polymer bead to the stationary intermediate walls or the base of the unattached parts and possibly also to the wedge parts. When mounted, the roll presses the polymer acting as a spring and the polymer generates a force which presses the roll tightly against the slanted surface. Between the roll and the polymer may be a separating support means which transmits the force of the spring. The spring may also be of metal.

To facilitate assembly, successive wedges or rolls can be mounted in successive mounting frames which are pressed together without clearance during mounting. In that case, the wedges or rolls of the rod or tube acting on the same face are in a different mounting frame, but the opposite means acting on the same point of the rod or tube may preferably be in the same mounting frame. After assembly, the mounting frames are pressed into their final position successively in such a way that there is no significant clearance between them. During operation, no significant forces are exerted on the frames to separate them and thus the absence of clearance is easy to achieve provided that the faces of the mounting frames resting on one another are smooth and straight.

There may be, for example, two or four rolls or wedges in one mounting frame, preferably two rolls acting on a flat rod, four rolls, that is, two opposite pairs acting on a rectangular rod. Alternatively, as a counter-pair of the roll can also be used a mere straight surface. Each of the rolls in a group has its own biasing spring which is arranged in such a way that the spring allows the rolls to be mounted in the mounting frame in connection with the assembly of the device, one mounting frame at a time, and then moving the mounting frames in one direction by moving them without clearance into their final position, where they are pressed or connected in succession, whereupon the successive mounting frames together form several successive locking means in the direction of movement.

The springs may be welded to the mounting frames in advance, in which case, when assembling the mounting frame on the rod, the rolls can be passed from a gap between the end of the rod and the spring, or the rolls can be kept in place before mounting by means of a suitable tool which keeps the rolls in place until the rod or tube keeps them in their final position. The tool may be, for example, a device in the shape of a locking rod, possibly additionally with means supporting the rolls which keep the rolls in place even if the rod and the tool are not completely in line during mounting. The supports may be, for example, spring-loaded pushers which extend at least to the end of the tool in such a way that even if the tool is moved slightly sideways, the rolls remain firmly pressed in place until the front edge of the bar supports the rolls in place and displaces the supports. The tool may also comprise means for keeping the rolls in place during mounting, in which case the rolls are placed on the tool and the tool is pushed into the mounting frame, whereupon the springs of the mounting frame stop the rolls in place when pushing the tool inside the mounting frame. After this, the mounting tool is pushed with the rod through the mounting frame and the rolls lock the mounting frame to the end of the rod.

If the springs have been shaped into suitably arched or inclined form before the springs are stressed, the rolls remain on the springs of the mounting frame, which is positioned spring downwards, by the effect of gravity. The mounting frame and the spring are then placed horizontally, for example on a table, in such a way that the spring is against the table. After this, the rolls are set in place on the springs, under the peak formed by the angle of the wedge plane. After this, once all rolls are in place, the locking means is picked up on the rod by pressing the rod between the rolls in contact with the table. The springs are thus biased very uniformly on all sides and mounting is quick and easy. The locking plane remains fixed right at the tip of the rod because the free direction of movement is from the table upwards. After this, the following mounting frame can be mounted in a corresponding manner on the rod, whereby the frames settle in succession on the rod. The inner locking means can be mounted inside the tube in a corresponding manner, one at a time, in succession.

The springs supporting the rolls are preferably plate-like torsion springs which can be welded into place in the body, or the springs can also be constructed so as to act as a locking ring, in which case for example springs with four rolls are parts of the same locking ring and the entire ring locks with spring force in a suitable groove or in clamps. If the spring is not welded, but is an unattached part at the assembly stage, the assembly can be carried out by mounting the spring only after the mounting frame and rolls. The advantages of the torsion spring are simplicity and flatness. A spring made of a steel strip is in addition durable and slippery and does not interfere unnecessarily with the turning of the roll. As a spring can also be used, for example, an undulated spring washer, which also functions as a torsion spring, but rests on the opposite surface, that is, for example the next mounting frame.

The mounting frames and their springs can also be constructed in such a way that they will also keep the rolls or wedges of even an unattached mounting frame in place. For this purpose, there is a support on the opposite side of the wedge surface of the rolls with respect to the springs, which prevents the roll from moving further. In addition, either the support or the spring can be designed to hold the rolls. The support may be, for example, a ring which is wedged on the wedge surface behind the rolls, or the support may be a fixed part of the mounting frame. In order for the roll to remain in place, the contact surfaces of the spring and the support with the roll must be further than within the radius of the roll from the wedge surface. The support may also have a cup-like shape. The support may also be removable once the mounting frame has been mounted in place. The removable support is preferably designed in such a way that it will not fit inside the device, but has to be removed in connection with the mounting. The removable support may be, for example, plastic.

The mounting frames are preferably smooth and shiny at their end parts which are in contact with one another in order that no clearance is formed between them. By means of separate successive frames, the assembly is easier to carry out and the successive mounting frames are pressed tightly against one another during use because no pulling forces are exerted on them, and thus the separate frames do not reduce the strength and solidity of the device, because essentially only compressive force, and to some extent torsional forces, are exerted on the mounting frames externally, if the rest of the structure of the device does not receive them. The mounting frames can also be welded to one another in connection with the assembly to rigidify the structure.

Since each mounting frame can preferably be made of one piece of material, they can be constructed to be extremely solid in the direction of the supporting forces of the locking means, in which case the clearance of a single locking means is as small as possible and there are no joints in the direction of the force generated by highest force of the locking means, that is, the force generated by the wedge surface or the sprag. The simplest mounting frame is the shape of a thick ring, there are slanted wedge surfaces for the rolls in the hole for the rod, and there may be a mounting recess for the springs, which gives them suitable flexibility. The recess giving flexibility may also be in the next mounting frame. In the frame are not needed any such parts that are not otherwise needed in the device. For example, compared with FIG. 1, the mounting frame may be considerably shorter and no stopper is required. Furthermore, a torsion spring takes up less space than a polymer spring. It is possible to make the mounting frame only slightly longer than the diameter of the rolls.

To facilitate assembly, the many successive rolls can also be glued to the unattached parts with a biocompatible substance. A suitable adhesive may be, for example, a resilient biocompatible silicone plastic which later acts also as a spring generating the bias force for the rolls or wedges. In that case, for example, silicone is used to glue the rolls on the slanted surface in such a way that the gluing simultaneously acts as a pressure spring during later operation. In practice, the back of the wedge then has to be shaped or roughened in such a way that the gluing or plastic casting will remain reliably fixed to the wedge part. The roll or sprag itself may detach from the gluing as soon as the assembly of the device has been completed. It is also possible to use, for example, water ice for temporary joining, which is easy to remove after the assembly by heating. In that case, the spring force must be generated in a different manner.

Between the roll or wedge and the polymer spring may be a separate support or bearing part which separates the spring and the roll from one another. This prevents the soft spring part from being twisted around the roll during use and thus the polymer from ending up between the friction surface. The support part may be temporarily connected to the roll for the duration of the assembly or the support part may also be, for example, mounted on a bearing at the end of the roll. If a sprag is used, the sprags can be glued with the resilient material acting as a spring in such a way that the gluing keeps the wedges almost in place at one end and at the same time generates biasing force during use. In such a case, a suitably designed counterpart can be used for the wedges. If the rolls are glued with a resilient polymer on a slanted surface or a support structure, they may also act as non-rotating wedges. In that case the position of the rolls will not change during operation, but when the locking is released, the polymer spring will return the position of the roll, which has twisted somewhat during locking, close to the original. The roll will thus probably become slightly flat on its friction surfaces during use, if plastic deformation or wear occurs in the roll.

Other preferable spring materials are steel, cellular rubber or cellular plastic and Nitinol, which is a well-known superelastic and biocompatible material.

Figure 3:
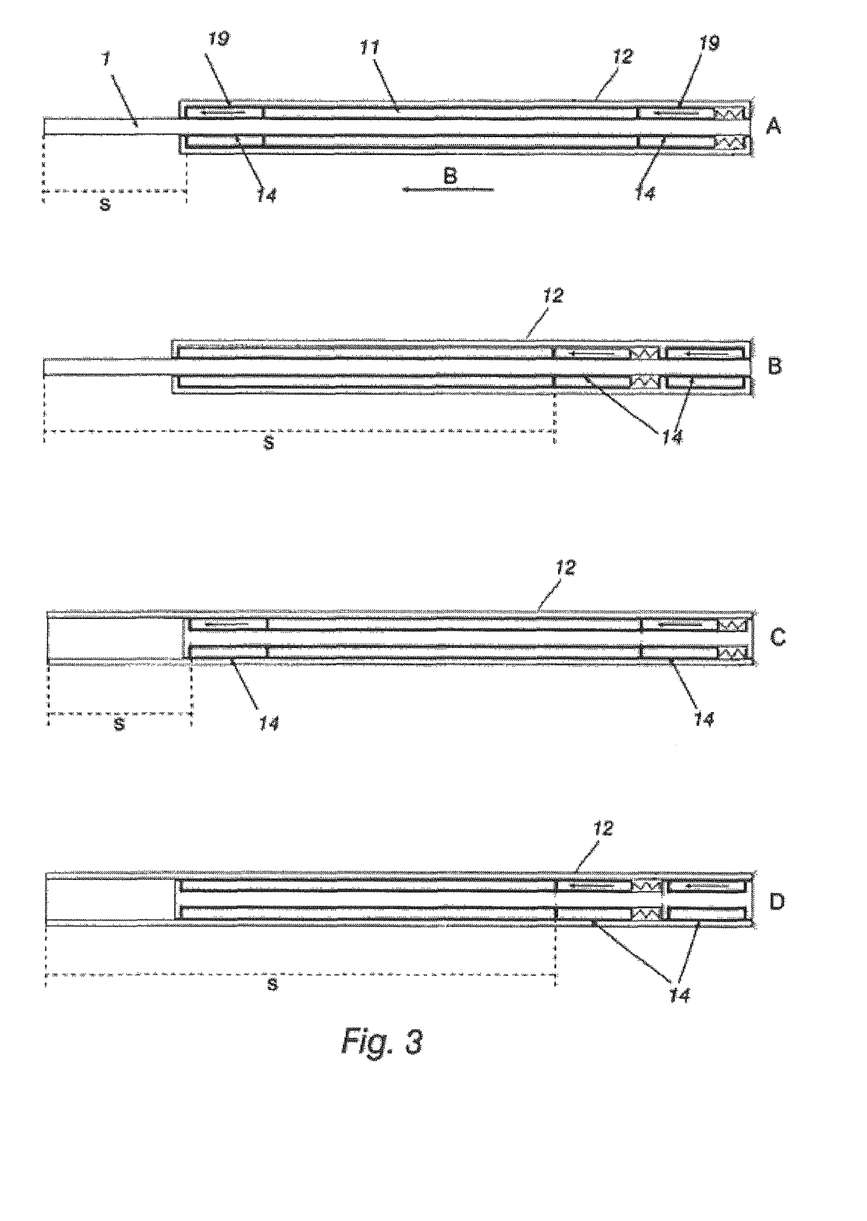
FIG. 3 shows different configurations for positioning the means allowing unidirectional movement.

FIG. 3 shows different positions of the means allowing unidirectional movement. In the first and third solutions (A and C), the means 19 allowing unidirectional movement are at different ends of a Terfenol means 11. In this case, the maximum path S is shorter than when the means 19 are on the same side, as in the second and fourth Figures (B and D). The locking friction surfaces 14 of the first two applications (A and B) are against the inner telescopic tube or rod 1 and friction surfaces 14 of the last two applications (C and D) act against the outer tube 12. Means arranged on the same side require an additional intermediate wall or support in the construction and thus the construction becomes somewhat more complex.

The rolls or wedges may only be on one side of the means moving in one direction. The roll or wedge will then press the moving means against the friction surface on the opposite side. This makes possible the use of different friction surfaces on the wedge or roll itself and its backing surface. The wedge or roll has to withstand much greater surface pressure than the frictional surface of a backing having a larger surface area. Also in that case, the wedging angle of the wedge or roll must be sufficient for locking the wedge or roll, but there does not have to be more than one wedge or roll. This is preferable not only from the point of view of manufacturing costs, but also because there will be deformation on only one side and thus high surface pressures causing clearance. This solution also makes possible a semicircular cross-section, in which case the friction surface of the backing is curved.

The invention claimed is:

1. An implantable treatment device adapted to be fixed or interlinked to bone, which generates unidirectional progressive movement by a member generating reciprocating motion in the same direction, using friction based means allowing unidirectional movement, the means allowing unidirectional movement comprising a second member disposed adjacent to an inner rod or an outer tube, the second member, or the inner rod or the outer tube, having a tapered portion having a slanted surface, wherein the tapered portion expands in the direction of movement of the inner rod or the outer tube, and wedge means disposed between the slanted surface of the second member, or the inner rod or outer tube, and a planar surface of the second member, or the inner rod or outer tube, extending parallel to the direction of movement of the inner rod or outer tube, the wedge means being selected from a group consisting of rolls, balls, barrel-shaped members or sprags, each wedge mean individually forming a line contact with the second member, or the inner rod or outer tube at a contact site with the line contact being substantially non-parallel to the direction of movement, wherein friction due to movement of the inner rod or the outer tube causes the wedge means to move to a first position of greater distance between the slanted surface and the planar surface when the inner rod or the outer tube is moved in the direction of movement, thereby allowing movement of the inner rod or outer tube in the direction of movement, and causes the wedge means to move to a second position of lesser distance between the slanted surface and the planar surface when the inner rod or the outer tube is moved against the direction of movement, thereby wedging the wedge means between the slanted surface and the planar surface at the line contact and preventing movement of the inner rod or outer tube against the direction of movement.

2. A device as claimed in claim 1, wherein there are several contact-making wedge means based on friction in succession in the direction of movement of the unidirectional movement.

3. An implantable device as claimed in claim 2, wherein groups of wedge means based on friction in succession in the direction of movement of the unidirectional movement are each mounted in their own separate mounting frames such that each mounting frame has its own biasing spring and the mounting frames are suitable for being mounted one at a time successively on a rod or tube, whereby the mounting frames can be moved, when the device is being assembled, in the direction of the allowed unidirectional movement to their final position along the rod or tube.

4. A device as claimed in claim 1, wherein at least one stationary counterpart of the balls, rolls or sprags is made as a separate part which is further connected to or rests by means of friction directly on its backing.

5. A device as claimed in claim 4, wherein several counterparts of the friction are arranged in succession in the direction of movement on one or more separate parts.

6. A device as claimed in claim 1, wherein the wedge means based on friction making line contact generates a frictional force resisting return movement in the part moving in one direction by at least pressing against a friction surface on a rear side of the reciprocating friction means.

7. A device as claimed in claim 1, wherein the member generating the reciprocating motion comprises a magnetostrictive, memory metal, MSM or piezoelectric means.

8. A device as claimed in claim 1, wherein the implantable treatment device is configured as an intramedullary bone extension device for disposition within a medullary cavity of a bone.

9. A device as claimed in claim 1, wherein the implantable treatment device is configured as an extramedullary treatment device for scoliosis or as a chin distractor.

* * * * *

UNITED STATES PATENT AND TRADEMARK OFFICE
CERTIFICATE OF CORRECTION

PATENT NO. : 9,474,612 B2  Page 1 of 1
APPLICATION NO. : 13/697654
DATED : October 25, 2016
INVENTOR(S) : Haaja et al.

It is certified that error appears in the above-identified patent and that said Letters Patent is hereby corrected as shown below:

On the Title Page

Item [87], should read:
PCT Pub Date: Dec. 1, 2011

Signed and Sealed this
Sixteenth Day of May, 2017

Michelle K. Lee
*Director of the United States Patent and Trademark Office*